(12) United States Patent
Schwendeman et al.

(10) Patent No.: US 12,226,524 B2
(45) Date of Patent: Feb. 18, 2025

(54) COATED IMPLANTS FOR LONG-TERM CONTROLLED RELEASE OF ANTIBODY THERAPEUTICS

(71) Applicant: THE REGENTS OF THE UNIVERSITY OF MICHIGAN, Ann Arbor, MI (US)

(72) Inventors: Steven P. Schwendeman, Superior Township, MI (US); Rae Sung Chang, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 293 days.

(21) Appl. No.: 16/097,977

(22) PCT Filed: May 2, 2017

(86) PCT No.: PCT/US2017/030642
§ 371 (c)(1),
(2) Date: Oct. 31, 2018

(87) PCT Pub. No.: WO2017/192590
PCT Pub. Date: Nov. 9, 2017

(65) Prior Publication Data
US 2019/0151237 A1 May 23, 2019

Related U.S. Application Data

(60) Provisional application No. 62/330,592, filed on May 2, 2016.

(51) Int. Cl.
| | | |
|---|---|---|
| *A61L 27/34* | (2006.01) | |
| *A61K 9/00* | (2006.01) | |
| *A61K 47/26* | (2006.01) | |
| *A61K 47/34* | (2017.01) | |
| *A61L 27/18* | (2006.01) | |
| *A61L 27/34* | (2006.01) | |
| *A61L 27/54* | (2006.01) | |
| *A61L 27/58* | (2006.01) | |
| *C07K 16/22* | (2006.01) | |

(52) U.S. Cl.
CPC .......... *A61K 9/0051* (2013.01); *A61K 9/0024* (2013.01); *A61K 47/26* (2013.01); *A61K 47/34* (2013.01); *A61L 27/18* (2013.01); *A61L 27/34* (2013.01); *A61L 27/54* (2013.01); *A61L 27/58* (2013.01); *C07K 16/22* (2013.01); *A61L 2300/252* (2013.01); *A61L 2300/256* (2013.01); *A61L 2430/16* (2013.01); *C07K 2317/24* (2013.01)

(58) Field of Classification Search
CPC .... A61K 9/0051; A61K 9/0024; A61K 47/26; A61K 47/34; A61L 27/18; A61L 27/34; A61L 27/54; A61L 27/58; A61L 27/505; A61L 2300/252; A61L 2300/256; A61L 2300/604; A61L 2300/622; C07K 16/22; C07K 2317/24

See application file for complete search history.

(56) References Cited

U.S. PATENT DOCUMENTS

| | | |
|---|---|---|
| 6,331,313 B1 | 12/2001 | Wong et al. |
| 2002/0009493 A1 | 1/2002 | Schwendeman et al. |
| 2007/0059336 A1* | 3/2007 | Hughes ................ A61K 9/0051 424/426 |
| 2014/0086974 A1* | 3/2014 | Wu ...................... A61K 9/0051 424/428 |
| 2015/0094641 A1* | 4/2015 | Park .................... A61F 9/00781 604/8 |
| 2015/0290092 A1 | 10/2015 | Shieh |

OTHER PUBLICATIONS

Zhou et al., Development of a Multiple-Drug Delivery Implant for Intraocular Management of Proliferative Vitreorinopathy,1998, Journal of Controlled Release, vol. 55, pp. 281-295. (Year: 1998).*
Zhong et al. Rescue of SCID Murine Ischemic Hindlimbs with pH-modified rhbFGF/Poly(DL-Lactic-co-Glycolic Acid) implants, May 23, 2007, Journal of Controlled Rlease, vol. 122, pp. 331-337. (Year: 2007).*
Amsden et al., A mechanistic study of the release of osmotic agents from polymeric monoliths, J. Controlled Release, 30(1):45-56 (Apr. 1994).
Amsden, Review of osmotic pressure driven release of proteins from monolithic devices, J. Pharm. Pharm. Sci., 10(2):129-43 (2007).
Andrew et al., Sustained Release of a Monoclonal Antibody from Electrochemically Prepared Mesoporous Silicon Oxide, Adv. Functional Materials, 20(23):4168-74 (Dec. 2010).
Chang, "PLGA Depots for Controlled Release of Bevacizumab", Dissertation, Doctor of Philosophy (Pharmaceutical Sciences), University of Michigan (2016).
International Application No. PCT/US2017/030642, International Search Report and Written Opinion, mailed Aug. 10, 2017.
Kang et al., Comparison of the effects of Mg(OH)2 and sucrose on the stability of bovine serum albumin encapsulated in injectable poly(D,L-lactide-co-glycolide) implants, Biomaterials, 23(1):239-45 (Jan. 2002).
Milacic et al., Lysozyme release and polymer erosion behavior of injectable implants prepared from PLGA-PEG block copolymers and PLGA/PLGA-PEG blends, Pharm. Res., 31(2):436-48 (Feb. 2014).
Yandrapu et al., Nanoparticles in porous microparticles prepared by supercritical infusion and pressure quench technology for sustained delivery of bevacizumab, Mol. Pharm., 10(12):4676-86 (Dec. 2013).
Zhu et al., Stabilization of proteins encapsulated in cylindrical poly(lactide-co-glycolide) implants: mechanism of stabilization by basic additives, Pharm. Res., 17(3):351-7 (Mar. 2000).

(Continued)

*Primary Examiner* — Ali Soroush
(74) *Attorney, Agent, or Firm* — MARSHALL, GERSTEIN & BORUN LLP

(57) ABSTRACT

Implants for anti-VEGF therapy provide both stability and controlled release of bevacizumab and other structurally sensitive polypeptides while maintaining protein/peptide stability in the micronized powder; achieving near zero order and complete release (>80%). Cylindrical implants suitable for intravitreal injection.

35 Claims, 9 Drawing Sheets

(56) References Cited

OTHER PUBLICATIONS

Zhu et al., Stabilization of proteins encapsulated in injectable poly (lactide-co-glycolide), Nat. Biotechnol., 18(1):52-7 (Jan. 2000).
European Patent Application No. 17793162, Extended European Search Report, dated Dec. 5, 2019.
Kang et al., Stability of proteins encapsulated in injectable and biodegradable poly(lactide-co-glycolide)-glucose millicylinders, Int. J. Pharm., 357(1-2):235-43 (Jun. 2008).

\* cited by examiner

COATED IMPLANTS FOR LONG-TERM CONTROLLED RELEASE OF ANTIBODY THERAPEUTICS

INTRODUCTION

Wet age-related macular degeneration (AMD) is a condition in which new abnormal blood vessels grow up and leak fluid or blood behind the macula. This leads to displacing the macula from its normal position, finally resulting in rapid central vision loss. AMD is the major cause of vision loss in the developed countries, especially in people aged 60 or older as expected from its name.

There are two forms of AMD: the wet and dry form. The wet form of AMD accounts for only 10% of the cases, but is responsible for 90% of vision loss, whereas the more common dry form results in relatively mild symptoms.

In wet AMD, the growth of abnormal blood vessels under the retina is stimulated by overexpression of vascular endothelial growth factor (VEGF). Therefore, anti-VEGF therapies have been developed to neutralize the overexpressed VEGF.

The first FDA-approved anti-VEGF agent was Macugen® (pegaptanib, anti-VEGF aptamer) which slowed vision loss compared with conventional treatment such as laser coagulation or photodynamic therapy, however it did not improve visual acuity in patients.

The next FDA-approved anti-VEGF agent for wet AMD was Lucentis® (ranibizumab, anti-VEGF monoclonal antibody Fab fragment), which until recently was the leading product in the market owing to its ability to improve visual acuity significantly in wet AMD patients.

On the other hand, Avastin® (bevacizumab, anti-VEGF whole monoclonal antibody), which is officially approved for certain types of cancer, has been used off-label extensively by clinicians because it shows similar efficacy to Lucentis® and because a single equivalent dose of Avastin® for wet AMD is 40 times less expensive than Lucentis®.

Finally, Eylea® (aflibercept, a recombinant fusion protein consisting of portions of human VEGF receptors 1 and 2 extracellular domains fused to the Fc portion of human IgG1) was recently approved for wet AMD in 2011 and is currently the most promising anti-VEGF agent since it can be less frequently administered. However, monthly intravitreal injection is very inconvenient for patients and repeated injections introduce risk of infection, inflammation and hemorrhage. Therefore, sustained release formulations are needed to reduce administration frequency for patient compliance and convenience and to minimize the risks by maintaining the therapeutic concentration longer in the target site.

Poly(lactic-co-glycolic acid) (PLGA) is among the most common and extensively researched polymer biomaterials, which has been used in several FDA-approved medical devices for controlled release formulations due to its biodegradability and biocompatibility. PLGA has been employed in a FDA-approved intravitreal injectable implant for controlled release of dexamethasone, which is Ozurdex®. The device is intravitreally injected by using a special pen-like applicator without any surgical incisions.

A drawback of PLGA formulations for protein encapsulation is formation of an acidic microenvironment during release due to the degraded acid byproducts in the polymer, which can destabilize the encapsulated proteins and result in incomplete release. This issue has been largely overcome by a combination of high protein loading and co-encapsulation of poorly soluble basic salts to neutralize the acids. This strategy has in many cases allowed a more continuous and higher total protein release. Similarly, the use of anhydrous microencapsulation when preparing devices in the millicylindrical form similar to Ozurdex® was developed by our group in order to minimize the stress during encapsulation of the organic solvent contact with a mobilized protein as occurs during common methods of encapsulation where dissolved protein makes contact with organic solvent. In order to encapsulate water-soluble proteins in PLGA implants, a micronized protein powder is first suspended in PLGA solution. Drying (e.g., lyophilization) and milling processes, which also can damage proteins, are needed to prepare protein powder for encapsulation. For the stability of encapsulated proteins, in addition, other osmolytes such as salts and sugars may need to be added, and these will affect the release kinetics of antibodies as well. Sugars such as trehalose and sucrose have been widely used in protein formulations as stabilizers. When too high amount of these osmotically active excipients are necessary in the formulation a problem arises that the biologically protein is released too fast.

SUMMARY

Implants for anti-VEGF therapy solve the above issues with formulating anti-VEGF protein dosage forms and other polypeptides. The formulation accomplished both stability and controlled release of bevacizumab while maintaining protein stability in the micronized powder; achieving near zero order and complete release (>80%); neutralizing acids liberated from PLGA for protein stability; optionally applying cryomilling for safely preparing protein powder for encapsulation; applying an anhydrous solvent extrusion technique to both stabilize the protein during encapsulation and to create cylindrical implants suitable for intravitreal injection; and applying a coating of biodegradable and biocompatible polymer to obviate the fast release caused by osmotic excipients necessary to stabilize the protein. While conventional PLGA formulations for sustained release have generally suffered from high initial burst release and a lag phase after the burst release, in particular embodiments, an encapsulated drug like bevacizumab, is continuously released from millicylindrical implants without high initial burst release and lag phase for up to eight weeks in vivo. Thus in particular embodiments, the current teachings are drawn to a solid implant for delivering polypeptides such as therapeutic antibodies. The implants are in the form of a cylinder or a millicylinder having a diameter of about 0.1 up to several millimeters and a length along a cylindrical axis greater than the diameter, for example, on the order of one to ten millimeters in length. The implant has a cylindrical inner portion that comprises a cylindrical surface and two ends, and the implant has a coating on the cylindrical surface of the cylindrical inner portion of the implant. The cylindrical inner portion contains a water soluble saccharide as a stabilizer, a polypeptide such as a therapeutic antibody or fragment thereof, a basic compound, and a biodegradable polymer such as poly(lactic-co-glycolic acid). The coating also contains optionally poly(lactic-co-glycolic acid), which is advantageously of the same composition and molecular weight as the poly(lactic-co-glycolic acid) of the cylindrical inner portion. Implants according to the current teachings have a loading of antibody preferably greater than about 5% by total weight of the implant. The implants are configured to deliver up to 80% or more of the antibody that is in the implant over its useful life. Advantageously, the polypeptide or therapeutic antibody retains at least 80% of its activity during its release lifetime, as measured by immunological techniques such as enzyme-linked immunosorbent assay (ELISA). In various aspects, it was not expected that one could accomplish both polypeptide/protein stability and slow and continuous release from such a preparation. Another advantage is that release kinetics are accomplished from a system that should largely disappear within a few weeks after release has ended. This is desirable for chronic delivery when implant accumulation can arise if too slow-degrading polymers are used (i.e., when release occurs much faster than erosion of the delivery system).

DRAWINGS

FIG. 1 is a graph that shows in vitro release kinetics of bevacizumab from implants prepared with original Avastin® powder (solid line) and buffer-exchanged bevacizumab powder without trehalose (dashed line). Theoretical loadings of each formulation were 3% (●), 6% (○), 10% (▼), 15% (Δ) and 15% (■). Symbols represent mean±SD, n=3.

FIG. 2 shows soluble bevacizumab recovered as a function of the amount of trehalose in the formulation. Cryomilled powder was prepared with the different ratio of trehalose to bevacizumab (w/w). Each bar represents mean±SD, n=3.

FIG. 3 shows release kinetics of bevacizumab from implants prepared with buffer-exchanged bevacizumab powder with the ratio of 1.5 to 1 w/w trehalose:bevacizumab. Theoretical loading of each formulation was 3% (●), 6% (○), 10% (▼), and 15% (Δ). Symbols represent mean±SD, n=3.

FIG. 4 shows in vitro release kinetics of bevacizumab from uncoated (●) and coated (○, ▼, λ) implants prepared with 10% initial theoretical loading of buffer-exchanged bevacizumab powder with 1.5 to 1 w/w/trehalose:bevacizumab (solid lines) in the core implants. Concentrations of PLGA in acetone solution for coating were 10% (○), 30% (▼), and 50% w/w (Δ). The long-dashed line (■) represents release kinetics from implants coated with 50% PLGA solution over 15% initial loading of the 1.5:1 powder in core implants. The dotted line (♦) represents release kinetics from implants coated with 50% PLGA solution over 10% initial loading of the original Avastin composition in the powder of the core implants. Symbols represent mean±SD, n=3.

FIG. 5 shows stability of bevacizumab during encapsulation and in vitro release from coated PLGA implants. Monomer content (A) and immunoreactivity (B) of released bevacizumab from implants coated with 30% w/w/PLGA (●) and 50% PLGA (○). Symbols represent mean±SD, n=3. CD spectra (C) of bevacizumab from intact Avastin® solution, 1:5 powder, extracts and release samples of 30% PLGA coated implants. Total peak area of the protein in SEC-HPLC was used to normalize all data.

DESCRIPTION

Figure 1:
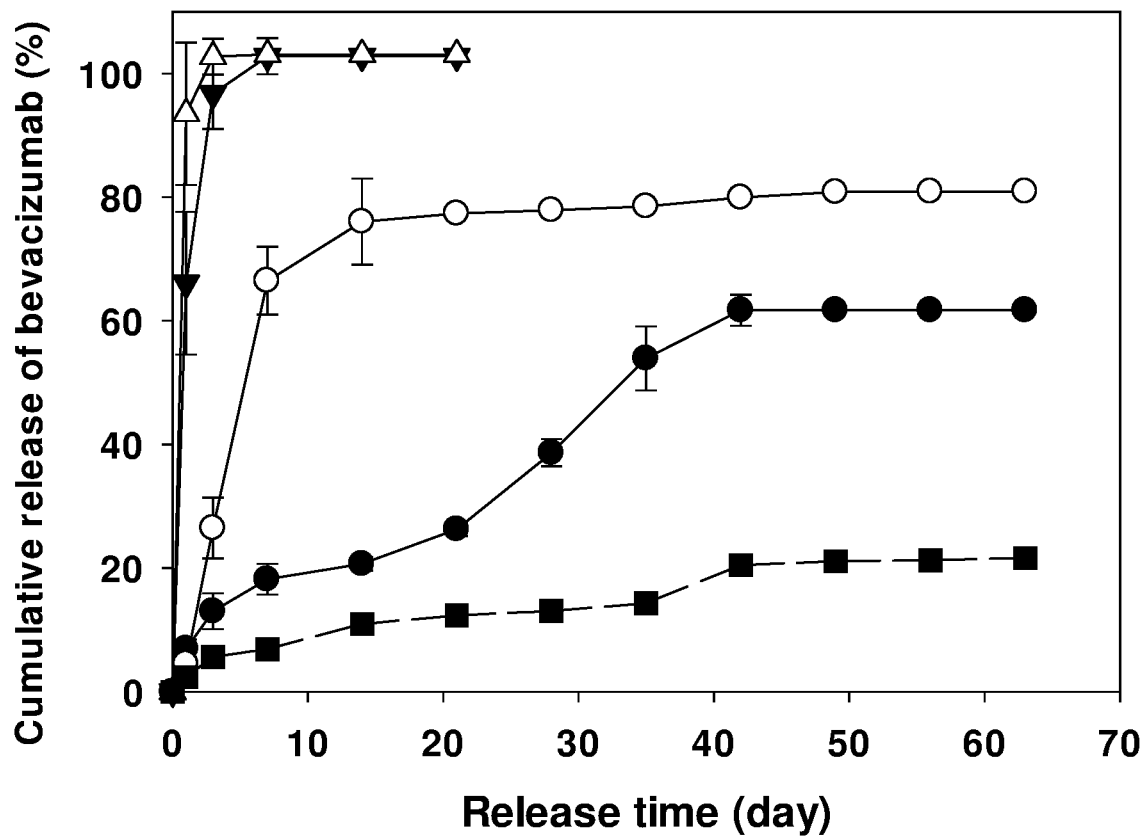

In one embodiment, a method of making an implant to deliver a polypeptide to a tissue involves providing a powder composition comprising the polypeptide; and combining the powder composition with a solution comprising a first biodegradable polymer in an organic solvent to make a suspension. The resulting suspension comprises the biodegradable polymer and the organic solvent, as well as a stabilizer and a basic material. The stabilizer is for example a water-soluble saccharide, while the basic material is characterized by having a solubility in water of about $2 \times 10^{-2}$ M or lower when measured at room temperature or at about 25° C. The suspension is then dried to remove the organic solvent and form a core. The method then involves applying a coating of a second biodegradable polymer on the core.

In this and other embodiments, at least one of the first and the second biodegradable polymer is poly(lactic-co-glycolic acid), for example one wherein the molar ratio of lactic to glycolic acid in the biodegradable polymer is 1:1. In some embodiments the first biodegradable polymer is the same as the second biodegradable polymer. In exemplary fashion herein, the stabilizer is a disaccharide, such as for example trehalose or sucrose. Other variations include those wherein the weight ratio of soluble saccharide to polypeptide is from about 0.3:1 to about 2:1. In exemplary methods, the solution of the first biodegradable polymer comprises 10% to 50% by weight of the first biodegradable polymer.

Further, in various preferred aspects of these embodiments, the method involves extruding the suspension into a conduit before drying. The conduit is silicone tubing, which is permeable to the solvent used to dissolve the polymer, in a non-limiting example. In particular aspects, the powder composition comprises the water-soluble saccharide before combining with the solution. Similarly, in certain aspects the solution comprises the basic material before combining with the powder composition.

In various aspects of the methods described herein, applying the coating on the core involves extruding a solution comprising a non-aqueous solvent and the second biodegradable over the core and removing the solvent in situ.

In further aspects, the basic material used in the methods comprises magnesium carbonate, magnesium hydroxide, or zinc carbonate. The polypeptide in various aspects is a protein, and can be selected from monoclonal antibodies. In a preferred embodiment, the polypeptide is one that binds vascular endothelial growth factor. In various embodiments, the polypeptide is thus an antibody, antibody fragment, or fusion protein that recognizes and binds to VEGF. Bevacizumab is one such agent.

In another embodiment, the current teachings provide a method of making an implant to deliver specifically bevacizumab to a tissue. the method involves providing a powder composition comprising bevacizumab and trehalose, wherein the weight ratio of trehalose to bevacizumab is from about 0.3:1 to about 2:1, and then combining the powder composition with a solution of poly(lactic-co-glycolic acid) in an organic solvent to make a suspension, wherein the suspension also comprises a basic material. The method then provides for extruding the suspension into a conduit and then drying the suspension in the conduit to remove the organic solvent and form an elongated core in the conduit. In addition, the method calls for applying a coating on the core by extruding a solution comprising a solvent and poly(lactic-co-glycolic acid) over the core and removing the solvent from the solution. In preferred embodiments the method further comprises removing the core from the conduit and cutting the core into a plurality of cylindrical implants.

In particular aspects, the suspension comprises 1% to 15% by weight of bevacizumab, or the basic material comprises magnesium carbonate, magnesium hydroxide, or zinc carbonate.

In certain embodiments described herein, a core containing a polypeptide is formed from a solution containing, in addition to the polypeptide, a biodegradable polymer and other excipients such as a soluble polysaccharide and a basic compound. In particular embodiments, the core is cylindrical by virtue of being extruded in solution form into a cylindrical conduit and then dried to remove the solvent and form the core. In various other embodiments, the core is formulated without the solvent and is solid-extruded or formed by direct compression (such as in a tablet press, in a non-limiting example) to form a core that is either later or simultaneously provided with a coating comprising a biodegradable polymer such as PLGA.

In a particular embodiment, a method of making an implant to deliver a polypeptide to a tissue, comprises a) providing a powder composition comprising the polypeptide; b) combining the powder composition with a mixture comprising a first biodegradable polymer, wherein the combined mixture comprises the polypeptide, the biodegradable polymer, a stabilizer comprising a water soluble saccharide, under anhydrous conditions (e.g., water content of final polymer matrix <1% w/w), and a basic material, wherein the basic material has a solubility in water of $2 \times 10^{-2}$ M or lower at room temperature; c) forming the combined mixture into a uniform dry polymer matrix in a shape suitable for drug delivery; and d) applying a coating of a second biodegradable polymer on the dry polymer matrix.

In various aspects, the method provides for (1) forming separately a core matrix with the listed elements (including the polypeptide, saccharide, biodegradable polymer, and basic compound) and then (2) applying the coating, wherein steps (1) and (2) can be carried simultaneously or in sequence. When the core is formed without solvent, normal solid extrusion can be used, and the core can be take on other geometrical shapes rather than just a cylinder.

In various embodiments, the core contains a relatively high level of osmotic excipients to provide for stability of the polypeptide but not so high as to compromise release kinetics upon coating of the core. In certain aspects, the dry polymer matrix suitable for drug delivery releases greater than 50% of the polypeptide in the first week under standard release in PBST at 37 C, or saccharide is at a loading as high as the polypeptide and the polypeptide is at a loading higher than 3% or higher than 5% w/w in the core.

In another embodiment, the methods provide a solid implant for delivering polypeptides such as therapeutic antibodies, in the form of a cylinder having a diameter 0.1 to 10 mm, preferably 0.1 to 5, more preferably 0.1 to 2 mm and having a length along the cylindrical axis of 1 to 30 mm or 1 to 20 mm or 1 to 10 mm, preferably about 2 to 10 mm or about 2 to 8 mm. Implants of these dimension are suitable for surgical implantation in the eyes, for example to treat a patient with wet age-related macular degeneration.

Larger implants are provided for use or implantation in locations that provide more room for the implant. Larger implants can be placed in tissues or in organs, or can be placed in the vicinity of tumors. Such implants can deliver therapeutic compounds to tissues in the brain, in a non-limiting example. If the size is not limited by the dimension of the tissue or organ into which it is to be implanted, the implant can have a diameter of 1 to 10 mm, or even 1 to 20 mm or 1 to 30 mm. In non-limiting fashion, the length of such implants can be longer 1 cm up to several cm long, for example 1-10 cm, 1-5 cm, 2-10 cm, 2-5 cm, and so on.

The implant contains a cylindrical inner portion comprising a cylindrical surface and two ends and a coating on the cylindrical surface with the ends either exposed or coated. The cylindrical inner portion comprises a water soluble saccharide, an antibody or antibody fragment that binds vascular endothelial growth factor (bevacizumab in a preferred embodiment), a basic compound, and poly(lactic-co-glycolic acid), and the coating comprises poly(lactic-co-glycolic acid).

In preferred aspects, the implant is characterized by one or more—up to all three—of having a loading of antibody greater than 5% by total weight of the implant, being able to deliver at least 80% of the antibody in the implant over its lifetime in an in vitro test, and the antibody or fragment thereof retaining at least 80% of its activity throughout the duration of the in vitro test, measured by ELISA. The water-soluble saccharide is trehalose in a preferred embodiment. As a result of the step of removing the core from the conduit and cutting the core into a plurality of cylindrical implants, in various embodiments there is no coating on the two ends of the cylindrical inner portion unless a second coating were to be applied.

In various embodiments, the delivery systems are characterized by how they perform in in vitro or in vivo tests. Examples of performance achieved by the delivery systems includes >90% monomer in release media over 42 days release; <20% initial burst and then over 80% released slowly and continuously over 42 days, >75% immunoreactivity in release media over 42 days release, and so on. In various embodiments, the systems are characterized by favorably low initial bursts (for example less than 30% or less 20%), favorable delivery of more than 70%, more than 80% or more than 90% of the encapsulated active material, and retention by that active material, if it is an antibody, of a favorably high amount of its immunoreactivity, such as >60%, >70%, >80%, or >90%.

In still other embodiments, the implant has a loading of an anti-VEGF antibody, or VEGF-binding polypeptide or protein, greater than about 5% by total weight of the implant, the implant is configured to resist 1 μg VEGF challenge for 8 weeks following intraocular injection of the implant containing a 400 μg or less dose of the anti-VEGF medicine.

In another embodiment, a method of treating wet age related macular degeneration in a patient, involves inserting any of the implants described herein into the eye of patient suffering from or diagnosed with wet macular degeneration.

These teachings provide delivery systems that can be used as implants, as well as methods for making the delivery systems. The teachings also provide methods of using those implants to treat medical conditions such as wet macular degeneration. As disclosed in part above and further below, the embodiments, whether they recite implants, methods for making the implants, or methods of using the implants, are characterized as a combination of various further aspects or limitations of the respective methods, implants, or methods of use. It is to be understood that limitation or aspect recited or specifically taught for one of the embodiments disclosed herein is also applicable to other embodiments, as though explicitly described for every embodiment.

Among these aspects or further limitations are the nature of the encapsulated active material, the nature of the biodegradable polymer, the stabilizer, the identity and nature of the basic material, the organic solvent used to make suspensions, as well as details of various aspects of the drying step that removes the solvent from either the core or the coating on the core, and aspects of forming the core by extruding into a conduit, etc. In addition to the aspects mentioned above, the following is a non-limiting description of further aspects.

Nature of the Encapsulated Active Ingredient

In its broadest sense, the current teachings provide methods for encapsulating a polypeptide active ingredient. The polypeptide is preferably one that can be stabilized with the use of the stabilizer described herein. In particular embodiments, the polypeptide is in the form of an antibody material including a monoclonal antibody, a fragment of an antibody material, or an antibody fusion protein. In various aspects, the polypeptide is one having affinity for vascular endothelial growth factor (VEGF). As further explained herein, the activity of the polypeptide as an anti-VEGF factor gives rise to the usefulness of an implant containing the polypeptide to treat wet age-related macular degeneration in patients. Specific examples include, without limitation, bevacizumab, ranibivumab, and aflibercept.

Biodegradable Polymer

A biodegradable polymer is used in the core and the coating of the implants described herein. A preferred biodegradable polymer is a homo-polymer or a co-polymer containing a lactic acid and/or glycolic acid repeat units. In various embodiments, biodegradable polymers are characterized by the molar fraction of lactic acid and glycolic acid in the polymer. Non-limiting examples of copolymers of lactic and glycolic acid (abbreviated PLGA for short) include polymers with a lactic acid content of 100-50 mol % and a glycolic acid content of 0-50 mol %. Other embodiments include polymers with 75-100% lactide and 0-25% glycolide. PLGA polymers are available from many commercial suppliers in a range of molecular weights. Specific non-limiting examples of the polymers are given in the working examples below. Non-limiting examples of biodegradable polymers include poly(lactides), poly(glycolides), poly(lactide-co-glycolides), poly(lactic acid)s, poly(glycolic acid)s, poly(lactic acid-co-glycolic acid)s, polycaprolactone, polycarbonates, polyesteramides, polyanhydrides, poly (amino acids), polyorthoesters, polycyanoacrylates, poly(p-dioxanone), poly(alkylene oxalates), biodegradable polyurethanes, block copolymers of these with polyethylene glycol, as well as blends thereof. Particularly preferred carriers are formed as homopolymers or copolymers of poly(lactic-co-glycolic acid) ("PLGA"), where the lactide:glycolide ratio from (0/100 to 100/0) can be varied depending on the desired carrier degradation rate. Hence the "PLGA" term includes all polyesters built from lactic and/or glycolic acid monomers irrespective of end group or crystallinity and also includes those polymers prepared from lactide and or glycolide (e.g., via ring-opening polymerization) and those polymers prepared from lactic and glycolic acid (e.g., via direct condensation).

Stabilizer

In various embodiments, the stabilizer is a water-soluble saccharide. In various preferred embodiments, the stabilizer is a disaccharide. Non-limiting examples of disaccharide stabilizers include trehalose, sucrose, lactose, mannose, and cellobiose. Trehalose is preferred in some embodiments.

Basic Material

The basic material used in the embodiments described herein is characterized as one of low solubility. Suitable basic materials are described, for example, in U.S. Pat. No. 6,743,446, the disclosure of which is incorporated by reference. Suitable basic materials include those that are sparingly soluble in water, as characterized by a solubility of about $2\times10^{-2}$ M or less, when measured at room temperature (which is taken as 25° C.). A saturated solution of the basic material in water is characterized by a pH of 6 or higher, and in preferred embodiments by a pH of higher than 7. Suitable basic materials include, without limitation, magnesium carbonate, magnesium hydroxide, magnesium oxide, magnesium trisilicate, zinc carbonate, zinc hydroxide, zinc phosphate, aluminum hydroxide, basic aluminum carbonate, dihydroxyaluminum sodium carbonate, dihydroxyaluminum aminoacetate, ammonium phosphate, calcium phosphate, calcium hydroxide, and the magnesium and aluminum complex known as magaldrate. Among these, magnesium carbonate, magnesium hydroxide, and zinc carbonate are preferred in various embodiments.

Organic Solvent

Suspensions are formed by combining a solution of the biodegradable polymer in an organic solvent with a powder made up of the polypeptide active material (also called the active pharmaceutical ingredient) and other components. The non-aqueous organic solvent is selected from any that dissolve the polymer, do not dissolve the powder, and can be removed to safe levels. The precise nature of the solvent is not overly critical, as it will be removed in a subsequent drying step. Suitable solvents include acetone, which does not significantly dissolve the protein and any of the solvents that are disclosed in the working examples below.

Drying Steps

The methods described herein provide for drying on two occasions. The first is after the suspension is extruded into a conduit such as a silicone tubing. The core is dried in situ in the conduit by simply placing the conduit in a heated oven, whereupon the solvent escapes out of the open ends of the tubing upon volatilization. To accelerate the process, the heating can be supplied under a vacuum. The combination of temperature and pressure can be adjusted to provide a suitable turnaround time.

Once the core is dried in the conduit, a solution of biodegradable polymer is extruded over the dried core in order to contact the core with the solution of biodegradable polymer. In an embodiment, the core is removed from the conduit and placed in another conduit before the step of contacting the core with the solution of biodegradable polymer is carried out in the new conduit. Afterward, the solvent is removed from the coating using the same kinds of steps as were used to dry the core. Suitable parameters of temperature, pressure, and time are described in the working examples.

Forming the Core

In various embodiments, the core is made by extruding a suspension containing biodegradable polymer and active polypeptide material, for example into a conduit. A suitable conduit is a silicone tubing, as further described herein. When the suspension is thus extruded into a silicone tubing, the configuration is one of a cylinder conforming to the shape and dimensions of the tubing. In preferred commercial embodiments, the tubing is provided with a circular cross-section so that the core takes the shape of a round cylinder.

In the alternative, the core can be extruded continuously and subject to a heat treatment for solvent removal, which can be coupled to a cutter to provide implants in a continuous process. After the core is coated as explained further herein, it is likewise dried to provide an elongated coated implant precursor in the conduit. In various embodiments, the implant precursor is removed from the silicone tubing and the elongated precursor cut into a plurality of shorter lengths to provide implants. In preferred embodiments, the implants are cut to a length of one to ten millimeters. In this way, implants are made that are in the form of a cylinder having a diameter equal to that of the silicone tubing and containing a cylindrical inner portion comprising a cylindrical surface and two ends, and further comprising a coating on the cylindrical surface. Because the implants are made by cutting an elongated implant precursor, it is seen that in certain embodiments, the ends of the cylindrical implant do not contain the coating that is applied on the rest of the cylindrical surface of the implant.

In a further alternative, the core can be formed by hot melt extrusion of a composition containing molten biodegradable polymer (such as PLGA); the antibody, antibody fragment, or fusion protein; the stabilizer; and the basic compound. The core is then coated with biodegradable polymer.

The configuration of the implant is such that the length of the cylinder axis is longer than the diameter of the cylinder, the latter of which conforms to the diameter of the silicone tubing used as conduit. In various embodiments, the diameter of the cylindrical implant is thus from 0.1 to 10 mm, preferably 0.1 to 5 mm, preferably 0.1 to 2 mm, or having particular values of about 0.7 mm or about 0.8 mm. The length along the cylindrical axis is greater than the diameter, such as 1 to 10 mm or preferably about 2 to 10 mm or about 2 to 8 mm. The size of the implant is selected in order that implanting it in the eye is enabled, and so that the implant contains a suitable therapeutic dose of the encapsulated polypeptide.

EXAMPLES

Example 1—In Vitro Studies of Anti-VEGF Antibodies

Materials

The Avastin®, commercial solution of bevacizumab was purchased from the pharmacy and used within its shelf-life period. PLGA 50:50 (inherent viscosity=0.64 dL/g and Mw=54.3 kDa, ester terminated) was purchased from LACTEL Absorbable Polymers (Birmingham, Ala.). Trehalose dihydrate (trehalose), $MgCO_3$, guanidine hydrochloride, DL-dithiothreitol (DTT), ethylenediamine-tetraacetic acid (EDTA), $Na_2HPO_4$, $NaH_2PO_4$, anti-human IgG-alkaline phosphatase antibody produced in goat and p-nitrophenyl phosphate liquid substrate system (pNPP) were purchased from Sigma-Aldrich Chemicals (St. Louis, Mo.). Tween 80 (10%), acetone, $KH_2PO_4$, $K_2HPO_4$, KCl, phosphate buffered saline (PBS), Amicon Ultra-15 Centrifugal Filter Units (10,000 MWCO), silicone rubber tubing, and Coomassie plus reagent assay kit were purchased from Fisher Scientific (Hanover Park, Ill.). Recombinant human vascular endothelial growth factor (VEGF) was a generous gift from Genentech.

Preparation of Bevacizumab Powder

The Avastin® solution containing bevacizumab and excipients was exchanged into 51 mM sodium phosphate buffer (pH 6.2) by using Amicon Centrifugal Filter Units (10,000 MWCO) to remove trehalose. Then, different levels of trehalose were added (weight of trehalose:weight of bevacizumab=0, 0.1, 0.5, 1 and 1.5:1) and the solution was diluted with 51 mM sodium phosphate buffer (pH 6.2) for the final bevacizumab concentration of 25 mg/mL and lyophilized. The solid was then ground by CryoMill (Retsch, Germany) at 30 Hz for 30 min and sieved through 90-μm screen (Newark Wize Wearing, Newark, N.J.). High trehalose content protein powder was prepared (ratio of 2.4 to 1, trehalose:bevacizumab) by lyophilizing the commercial Avastin® solution without buffer exchange, and then ground and sieved.

Preparation of Injectable Implants with Bevacizumab

The resulting bevacizumab powder was suspended into 50% (w/w) PLGA solution in acetone with 3% (w/w) $MgCO_3$ in a 2-mL centrifuge tube, then mixed and transferred into a 3-mL syringe. The suspension was extruded into silicone rubber tubing (I.D.=0.8 mm), then dried at room temperature for 48 h followed by vacuum drying at 40° C. and −23 in. Hg vacuum for an additional 48 h. The final dried implants were obtained by removal of silicone tubing and were cut into 1 cm long segments for future use. For coated implants, the core implants were put back into silicone tubing and pure PLGA solution at various concentrations in acetone within a 3-mL syringe was extruded over the core implants to coat the surface and dried in vacuum oven at room temperature for 48 h and at 40° C. for an additional 48 h. Then, silicone tubing was removed and the final coated implants were cut for the following experiments.

Measurement of Bevacizumab Loading in Implants

Implants (3-5 mg) were dissolved in 1 mL of acetone for 1 h and centrifuged to precipitate proteins. PLGA dissolved in supernatant was removed and the protein pellet was washed with acetone and centrifuged three times more to remove residual PLGA. The pellet was then air dried, reconstituted in 1 mL of PBST (phosphate buffered saline with 0.02% Tween-80, pH 7.4) at 37° C. overnight and analyzed by size-exclusion high-performance liquid chromatography (SE-HPLC). The condition of SE-HPLC to quantify monomer and soluble aggregates was followed as previously described (L. Liu, D. A. Ammar, L. A. Ross, N. Mandava, M. Y. Kahook, J. F. Carpenter, Silicone oil microdroplets and protein aggregates in repackaged bevacizumab and ranibizumab: Effects of long-term storage and product mishandling, Investig. Ophthalmol. Vis. Sci. 52 (2011) 1023-1034. doi:10.1167/iovs.10-6431) with slight modifications, which included the injection volume of 50 μL and filtration of all samples through 0.45-μm filter. Extracted loading and loading efficiency were calculated by the following equations.

$$\text{Extracted loading (\%)} = \frac{\text{Weight of extracted bevacizumab}}{\text{Weight of total implant}} \times 100\%$$

$$\text{Loading efficiency (\%)} = \frac{\text{Extracted loading}}{\text{Theoretical loading}} \times 100\%$$

In Vitro Release Study of Bevacizumab from Implants

Implants (1 cm long, 6-8 mg) were added in 1.5 mL centrifuge tubes with 1 mL of PBST and incubated at 37° C. without agitation, as agitation was found to cause insoluble aggregation of the antibody in the release media. The release medium was replaced with fresh medium at each time point. The amount of released bevacizumab at each time point was measured by SE-HPLC and calculated as percentage of the released amount out of the extracted loading of soluble bevacizumab. In certain instances, the release media was also analyzed for protein structure and immunoreactivity, as described below.

Evaluation of Residual Bevacizumab in Implants

At the end of release study, the remaining bevacizumab was extracted by the same procedure used to measure protein loading after lyophilizing the remaining polymer. The protein pellet was then reconstituted in PBST and incubated at 37° C. overnight to determine the soluble fraction of the protein remained in the polymer. After centrifugation, the supernatant was collected and the remaining insoluble precipitates were dissolved in denaturing solvent (6M guanidine hydrochloride/1 mM EDTA) at 37° C. for 1 h to determine non-covalent protein aggregates. After centrifuging and collecting supernatant, the remaining insoluble precipitates were dissolved again in denaturing/reducing solvent (6M guanidine hydrochloride/1 mM EDTA/10 mM DL-Dithiothreitol) to measure covalent protein aggregates formed by disulfide bonds. Concentration of protein aggregates in each step was measured by Coomassie plus protein assay. All measurements were performed in triplicate (n=3) and bevacizumab standards were dissolved in the same solvent used for each analysis.

Measurement of the Effect of Trehalose on Aggregation of Bevacizumab in Powders

Bevacizumab powder with the various ratios of trehalose to bevacizumab (0, 0.1, 0.5, 1, 1.5 and 2.4:1) were dissolved in PBST at 37° C. overnight. The soluble fraction of protein was measured by SE-HPLC to determine the effect of trehalose on aggregation of bevacizumab.

Enzyme Linked Immunosorbent Assay (ELISA)

The indirect ELISA was performed to determine immunoreactivity of the released bevacizumab as described previously (J. S. Andrew, E. J. Anglin, E. C. Wu, M. Y. Chen, L. Cheng, W.R. Freeman, et al., Sustained release of a monoclonal antibody from electrochemically prepared mesoporous silicon oxide, Adv. Funct. Mater. 20 (2010) 4168-4174. doi:10.1002/adfm.201000907) with some modifications. Briefly, 96-well ELISA microplates were pre-coated with 50 µl of VEGF (0.5 µg/mL) solution in PBS (phosphate buffered saline, pH 7.4) at 4° C. overnight. After washing with 350 µl of PBS four times, 100 µl of PBS containing 1% BSA (bovine serum albumin) was added for blocking and incubated at room temperature for 2 h. After washing, 50 µl of bevacizumab standards (0-2.56 µg/mL) and samples diluted in PBST containing 1% BSA were added into each well and incubated at room temperature for 1 h. After washing, 50 µl of secondary antibody (alkaline phosphatase conjugated goat anti-human IgG) was added at 1:1000 dilution in PBST containing 1% BSA into each well and incubated for another 1 h. Detection was carried out by adding 50 µl of pNPP after washing. Color development was monitored with a plate reader (Dynex MRX II, Richfield, Minn.) every 10 min for 30 min at 405 nm.

Circular Dichroism (CD)

CD was performed with Jasco J-815 CD spectrometer equipped with Jasco temperature controller (CDF-426S/15) and Peltier cell at 25° C. The samples were diluted or buffer-exchanged into 51 mM sodium phosphate buffer (pH 6.2) and concentrated by using Amicon Centrifugal Filter Units (10,000 MWCO), so the final concentration ranged from 0.05 to 0.5 mg/mL for far UV measurements. The samples were measured in quartz cuvettes (Hellma) with a path length of 1 mm. The spectra were collected in continuous mode at a speed of 50 nm/min, bandwidth of 1 nm and a DIT of 1 sec and were the averages of 10 scans. The spectrum of blank 51 mM sodium phosphate buffer (pH 6.2) was subtracted from each spectrum by using the Jasco spectra manager software (Version 2.1). The raw data was converted to mean residue ellipticity (MRE) using the following equation:

$$[\theta]_{mrw,\lambda} = MRW \times \frac{\theta_\lambda}{10 \times d \times c}$$

Where is the $\theta_\lambda$ observed ellipticity in degree at wavelength $\lambda$, d is the path length in cm, c is the concentration in g/mL, and mean residue weight (MRW) in g/mol is 113 for bevacizumab. Data smoothing was performed using Sigma-Plot software (Version 12.0, Systat Software, Inc.).

Evaluation of Bevacizumab Loaded Implants with Trehalose

Injectable PLGA implants were employed to sustain release of bevacizumab for local delivery. First, commercial Avastin® solution was lyophilized without any changes in its composition, ground and sieved to prepare the bevacizumab powder. The formulation of Avastin® originally contains trehalose whose amount is 2.4 times as much as that of bevacizumab, as shown in Table 1. Avastin® also contains small amount of polysorbate 20 and buffer salts as excipients, therefore, 3, 6, 10, and 15% loadings (w/w) of bevacizumab are equivalent to 11.1, 22.2, 37.0 and 55.4% loading of total protein powder, respectively. A poorly soluble base, $MgCO_3$ was also added into implants at 3% (w/w) as an antacid to stabilize loaded proteins by preventing low pH created by acid by-products from degradation of PLGA in implants during release (G. Zhu, S. R. Mallery, S. P. Schwendeman, Stabilization of proteins encapsulated in injectable poly (lactide-co-glycolide), Nat. Biotechnol. 18 (2000) 52-57. doi:10.1038/71916; V. Milacic, S. P. Schwendeman, Lysozyme Release and Polymer Erosion Behavior of Injectable Implants Prepared from PLGA-PEG Block Copolymers and PLGA/PLGA-PEG Blends., Pharm. Res. 31 (2013) 436-448. doi:10.1007/s11095-013-1173-6.). Loading efficiencies calculated from extracted loadings ranged from 92.2 to 99.6% (Table 2). Release rate of bevacizumab from these implants increased as protein loading increased (FIG. 1). In addition, the initial burst release on day 1 from 10 and 15% loaded implants, which were 66.1 and 93.5%, was significantly higher than one from 3 and 6% loaded implants, which were 7.0 and 4.6%. Therefore, there must be the percolation threshold between 6 and 10% protein loading which equates to 22.2 and 37.0% of total powder loading. Above the percolation threshold, the majority of drug particles are connected to each other and create water channels rapidly due to their high water solubility when water uptake starts, and then the drug molecules will be transported out fast through the rapidly formed water channels by diffusion and/or convection, thus creating high initial burst release and fast following release.

Below the percolation threshold, more drug particles are not connected in polymer matrix, and thus form isolated water pores when water dissolves the drug particles. The isolated water pores start to swell because osmotic pressure created by the osmotically active water-soluble components of drug powder induce more water uptake. Finally, the swollen pores are ruptured and form microcracks which connect the adjacent pores, and then the drug molecules can be released through the interconnected pores. These steps involved in the formation of channels with microcracks induced by osmotic pressure are relatively slower than those above the percolation threshold, thus acting as rate limiting steps (B. Amsden, Review of osmotic pressure driven release of proteins from monolithic devices., J. Pharm. Pharm. Sci. 10 (2007) 129-43. http://www.ncbi.nlm.nih.gov/pubmed/17706172); B. G. Amsden, Y. Cheng, M. F. A. Goosen, A mechanistic study of the release of osmotic agents from polymeric monoliths, 3659 (1994). Therefore, the initial burst release is relatively low and following release rate is also slow because it is driven dominantly by osmotic pressure. The implants loaded with 3% bevacizumab showed the most promising release profile which was continuous for 6 weeks with low initial burst and 61.7% of total cumulative release. The incomplete total release from implants with lower loading is attributed to less homogeneous diffusion of $MgCO_3$ into the pores formed by drug particles which creates some acidic pores by polymer degradation during release period, thus finally destabilizing proteins (Z. Gaozhong, S. P. Schwendeman, Stabilization of proteins encapsulated in cylindrical poly(lactide-co-glycolide) implants: Mechanism of stabilization by basic additives, Pharm. Res. 17 (2000) 351-357. doi: 10.1023/A:1007513425337). Most of the residual proteins analyzed by extraction were non-covalent aggregates, which was ~14% and total recovery was ~72% (Table 2). However, implants for intravitreal injection need higher loading due to the limit of injection volume of implants into vitreous and total cumulative release of ~62% still needs to be improved as the remaining protein aggregates have a risk of becoming immunogenic.

Evaluation of Bevacizumab Loaded Implants without Trehalose

Therefore, to reduce rapid release and increase protein loading, the osmotically active trehalose was removed by buffer-exchange before loading into the polymer. Without trehalose, only 59.9% soluble protein was recovered from the implant after encapsulation, which is equivalent to 9.0% extracted loading (Table 2). The implant showed very slow release during the whole release study period and released only ~22% bevacizumab out of the soluble extracted loading (or ~13% of theoretical loading) by the end of release, as seen in FIG. 1 and Table 3. To analyze the remaining protein in polymer, the antibody was extracted from the implants after the release study. Soluble residual protein in PBST, non-covalent aggregate and covalent aggregate by disulfide bonds were 1.3%, 40.3% and 1.6%, respectively, with a total recovery of only 56.2%. The remaining protein, which was not recovered, could have formed covalent non-disulfide bonds or hydrolysis products not analyzed by the SE-HPLC in the release media. Instability of bevacizumab during preparation of implants and the release study is thought to be attributed to the absence of trehalose in the drug powders since the loading efficiency and total cumulative release of the implants with the presence of trehalose were both higher.

Effect of Trehalose on Aggregation of Bevacizumab in Powders

Figure 2:
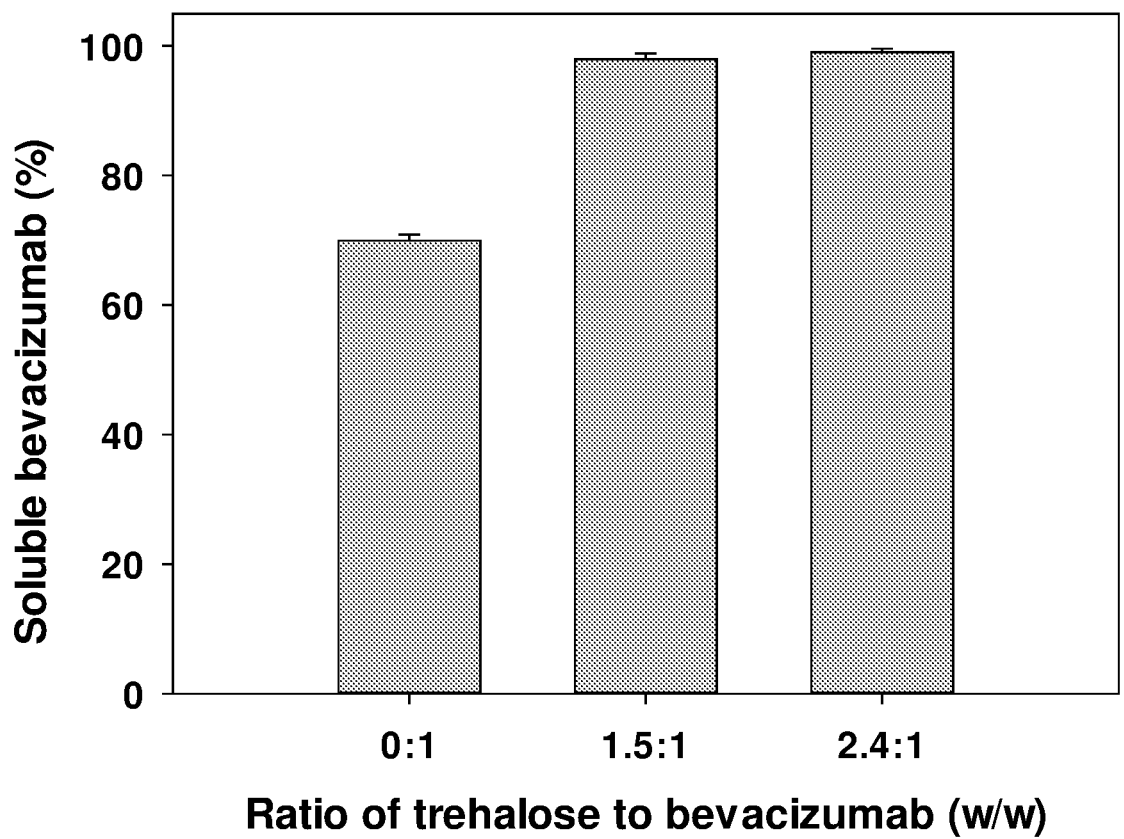

The presence of trehalose in the drug powder stabilized bevacizumab in the implants, but it also increased release rate undesirably since the commercial Avastin® has considerable amount of trehalose compared to bevacizumab, whose weight ratio is 2.4:1 (2.4:1 powder). Therefore, we sought to adjust the ratio so that both high stability and desirable release rate of bevacizumab would be possible at the same time. To determine the optimal ratio of trehalose to bevacizumab in the protein powder, buffer-exchanged bevacizumab was mixed with trehalose at various ratios before preparing the micronized drug powder, as used for encapsulation. Then, the soluble protein in the powder when dissolved in PBST was measured by SE-HPLC (FIG. 2, 6). The powder prepared from commercial Avastin® resulted in 99.1% recovery of soluble bevacizumab and 98.0% was recovered from the powders with the reduced ratio of 1.5:1 w/w trehalose:protein (1.5:1 powder). Further reducing trehalose in the powder at a trehalose:protein level of 1:1 resulted in only 76.3% bevacizumab solubilized and the absence of trehalose resulted in only 69.9% soluble protein in the powder. Therefore, the 1.5:1 powder was selected for the next step preparation of implants to maintain the stability of bevacizumab while slowing down the release.

Evaluation of Implants with Trehalose Content

Figure 3:
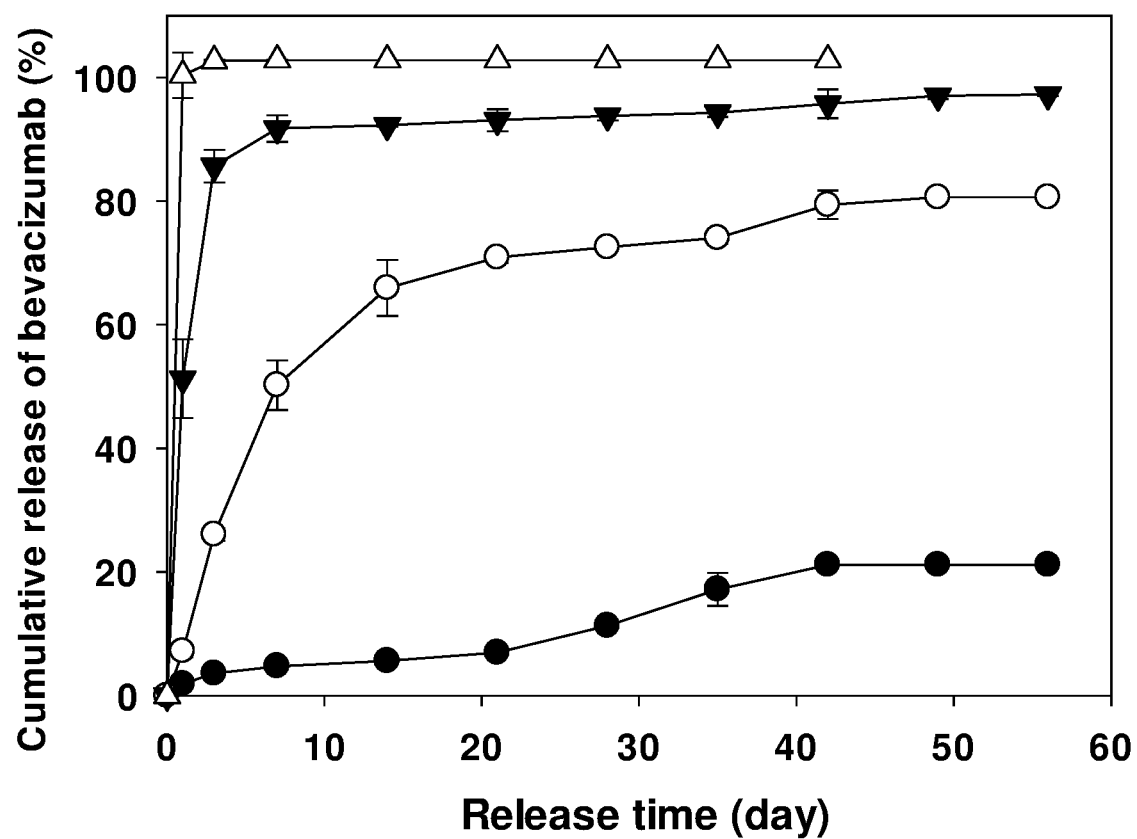

To compare release rate of the implants prepared with 1.5:1 w/w trehalose:bevacizumab powder to the previous set of implants with 2.4:1 powder, implants having the same loading of bevacizumab (3, 6, 10 and 15%) were tested. Loading efficiencies of extracted soluble bevacizumab ranged from 90.7-94.1%, which were slightly lower than the implants with 2.4:1 powder (Table 4). The release rate of each implant with the same bevacizumab loading as in the implants with 2.4:1 powder was slower as expected due to lower total powder loadings (8.3, 16.7, 27.8 and 41.7%, respectively) with reduced trehalose content (FIG. 3). Release rate from 3% bevacizumab loaded implant was very slow and total cumulative release was only 21.2% when it stopped on day 42. The implants loaded with 10 and 15% bevacizumab loading released their proteins very fast as expected because their total powder loading (27.8 and 41.7%) clearly exceeded the lower percolation threshold in the polymer matrix. From evaluating the initial release from the previous set of the implants with the 2.4:1 powder, the percolation threshold was likely in the range between 22.2 and 37.0% of total powder loading. The implant loaded with 6% of bevacizumab also showed low initial burst release (~7.2%) on day 1 since the total solids loading was lower than the assumed percolation threshold. Among this set of implants, one loaded with 6% bevacizumab showed the most promising release profile, although the release rate was not as constant as desired during the whole release period for an ideal formulation. Trehalose cannot be reduced any further due to instability of bevacizumab in the powder, and therefore, other strategies were needed to achieve higher loading and near zero-order release profile.

Figure 4:
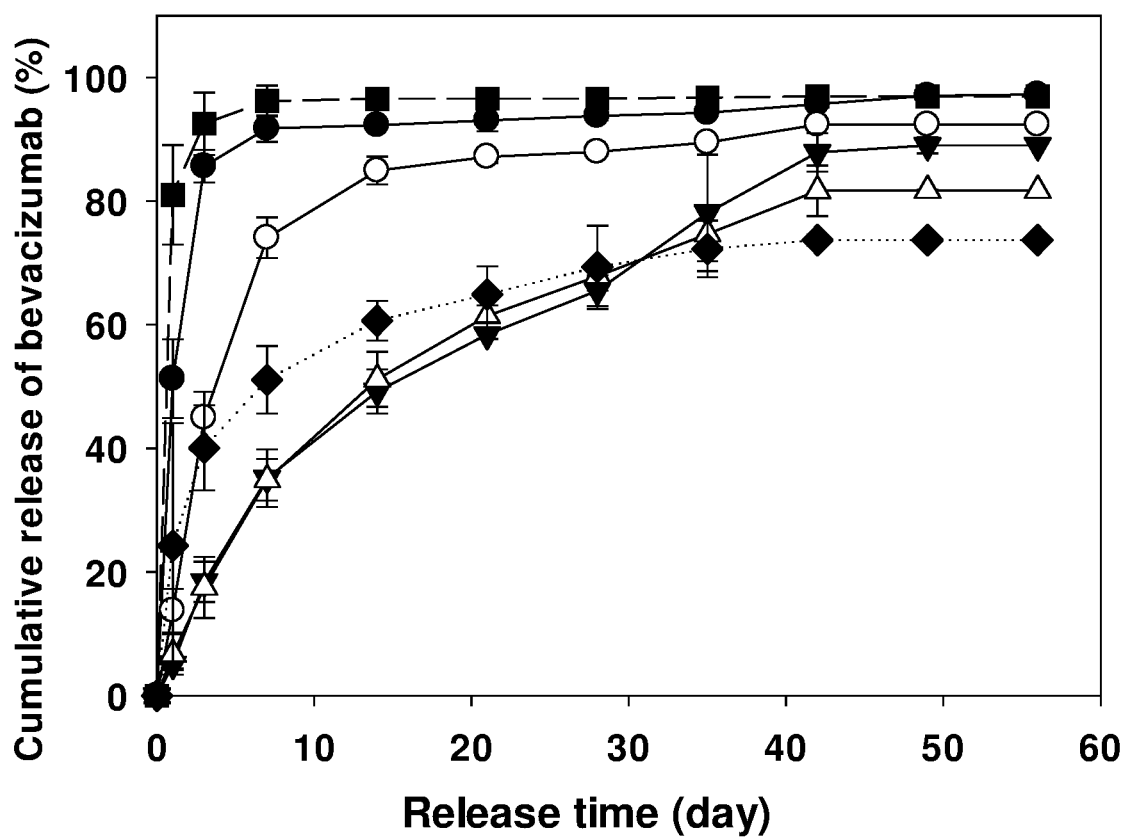

Coated Implants with Blank PLGA for Higher Loading and Improved Continuous Release The strategy of reducing trehalose in the drug powder had limitations for higher loading of bevacizumab and its sustained release. As a coating method, simply extruding pure PLGA over the core implants in silicone tubing was used and the degree of coating was controlled by PLGA concentration in coating solution. Since the loading of bevacizumab needs to be high after coating, only 10 and 15% loaded core implants were coated and tested. As a result of coating with pure PLGA and added polymer, the extracted loading of bevacizumab was lower than that of the core implants. Also as expected, a higher PLGA concentration in the coating polymer solution resulted in lower extracted loadings of bevacizumab and thicker diameters of implants (Table 5). As a core, 10% bevacizumab loaded implants with 1.5:1 powder were tested to determine how PLGA concentration in coating affected the release profile. All the coated implants released the drugs slower than their core implant, and higher PLGA concentration in coating resulted in slower release (FIG. 4). Coated implants with 10% PLGA showed slower release rate than the core implant and the implants coated with 30 and 50% PLGA released bevacizumab even slower than 10% coated one and showed close release profile to near zero-order for 6 weeks. The implants coated with higher PLGA concentration than 50% were not able to be tested because PLGA solution was too viscous to extrude over the core implants The release from the core implants loaded with 10% bevacizumab and 1.5:1 w/w trehalose: protein powder was fast and likely dominated by pure diffusion and/or convection through a network of percolating pores since the drug particles above the percolation threshold were interconnected rapidly. By coating the sidewall of core implants, fast release of bevacizumab located near the surface was expected to occur primarily through the both open ends, thus resulting in lower initial burst release. The initial burst release on day 1 reduced from 51.3% in uncoated implants to 13.8% in 10% PLGA coated ones, and 5.1 and 6.7% in 30 and 50% PLGA coated ones. The protein molecules located deeply into the middle of coated implants have a much longer distance to the surface of both ends than that in core implants whose maximum is only the radius of the core implants. Hence, it is possible that less complete channels from a drug particle to the surface in coated implants were formed even above the percolation threshold in core implants and resulted in low initial burst release and slower following release driven by slow formation of osmotic pressure-induced channels between pores. Release rates of 30 and 50% PLGA coated implants were similar during the whole release study period whereas release was faster in 10% PLGA coated implants. Thus, the coating formed from a 10% PLGA solution was likely not thick enough to effectively coat the core implants completely during release, while PLGA at 30% concentration or higher coat the core implants thick enough to prevent the release through the side walls before polymer mass loss occurs. However, 50% PLGA coated implants with 15% bevacizumab loading of 1.5:1 powder still showed very high initial burst release (81.0%) and almost complete release after day 7. At this total powder loading (41.7%) in core implants, most drug particles are thought to be interconnected due to their high proximity and porosity above the lower percolation threshold, thus enabling formation of water channels through the interconnected particles from both open ends rapidly once the implants are put in release medium. It is noted here that later studies in fact suggested unexpectedly the transport was not only occurring from the ends of the coated cylinder but also through pores evolved in the coating itself, which rapidly developed pores for mass transfer (data not shown). The coated implants with 10% core loading of bevacizumab with 2.4:1 powder was also tested as a control. As expected, the initial burst release was higher than the corresponding implant with 1.5:1 powder due to higher total powders loading in core implant and more interconnected drug particles. By coating implants with pure PLGA, therefore, 30 and 50% PLGA coated implants with 10% bevacizumab loading of 1.5:1 powder were the best formulations among all the tested formulations for higher loading (8.2 and 7.6%), more sustained release, and higher total cumulative release (89.0 and 81.7%). The major residual proteins in polymer were non-covalent aggregates, which were 7.8 and 8.9%, and total recoveries were 97.7 and 91.9%, respectively (Table 6). It is important to note that a small difference in recovery and complete release was observed be for the two different coating conditions. It is possible that the thinner coating (from 30% polymer concentration), which was also sufficient to maintain the release, was able to reduce the diffusion barrier to water-soluble acids relative to the thicker coating (50%), slightly increase the microclimate pH to reduce aggregation and hydrolysis of the protein.

Figure 5:
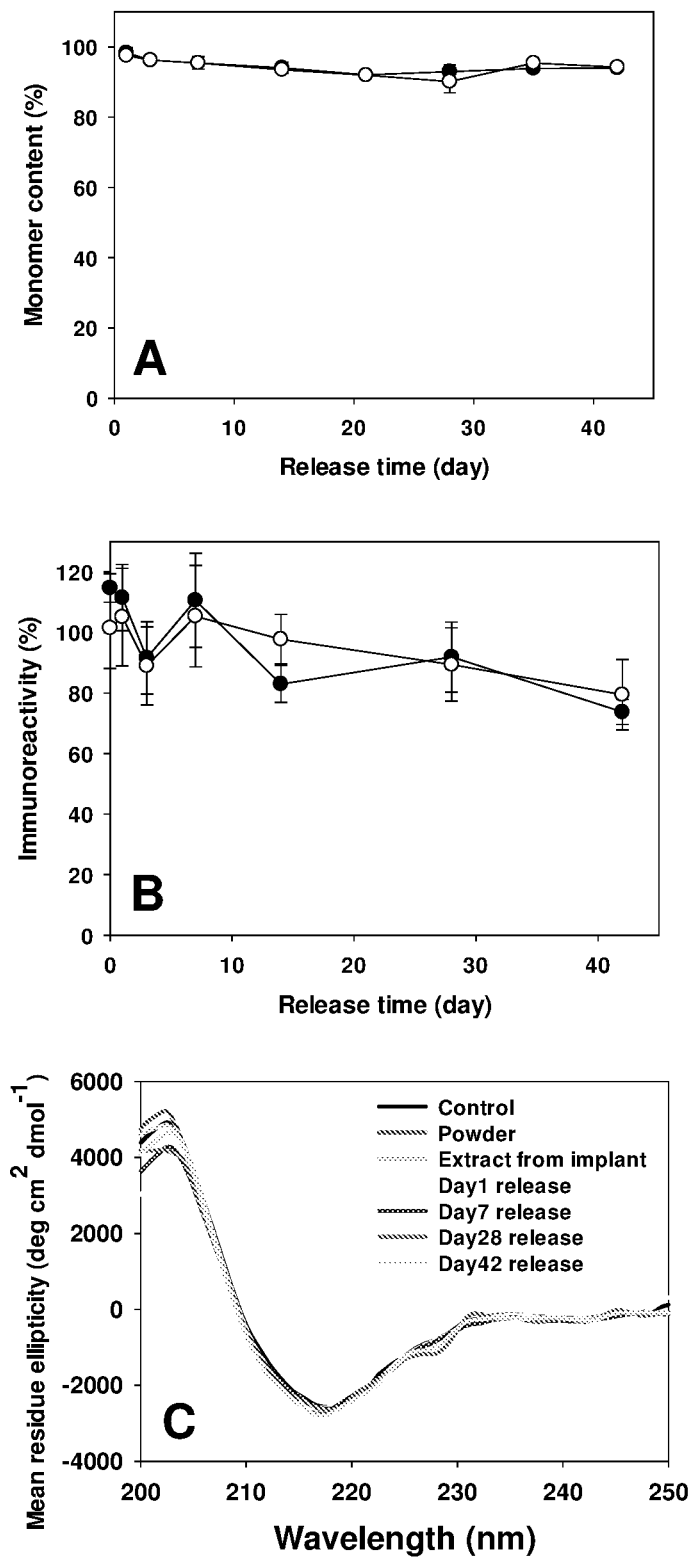
Figure 6:
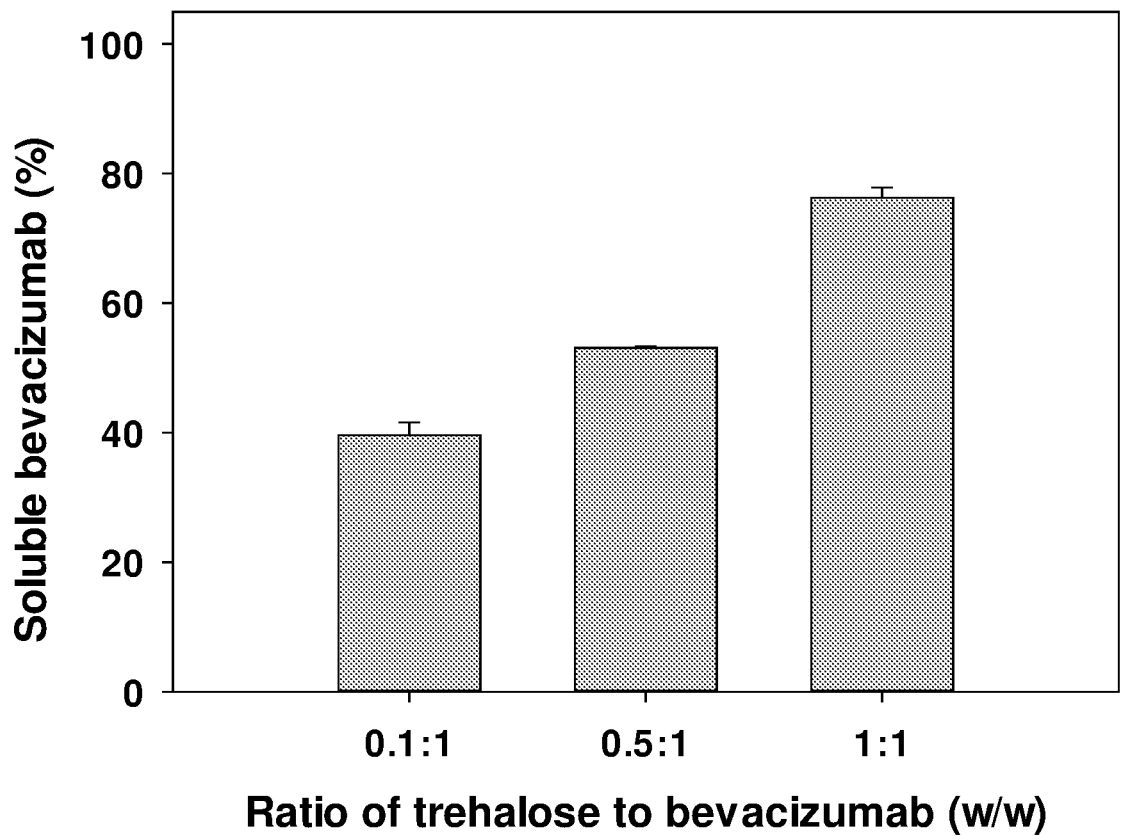
FIG. 6 shows soluble bevacizumab recovered from powder prepared with the different ratios of trehalose to bevacizumab (w/w) prepared on a small scale. Each bar represents mean±SD, n=3.

To investigate the stability of released bevacizumab from these implants, monomer content, immunoreactivity and conformational stability in secondary structure were evaluated via SE-HPLC, ELISA and CD. Intact bevacizumab originally shows a small dimer peak in size-exclusion chromatogram and the monomer content calculated by the following equation, $$\text{Monomer content (\%)} = \frac{\text{area of a monomer peak}}{\text{area of total peaks}} \times 100\%$$

is dependent on the concentration of bevacizumab. Released proteins from the formulations had a bit less monomer content than that of the corresponding concentration of intact bevacizumab, but it was maintained above 90% during the whole period (FIG. 5A). Until 3-4 weeks of release, the monomer content decreased and slightly increased thereafter. It is speculated that formation of soluble dimers or oligomers from monomers resulted in the early decrease in monomer content and consumption of the soluble aggregates as nuclei for growth of higher order insoluble aggregates trapped in polymer caused the later increase in monomer content. The immunoreactivity of extracted and released proteins from the coated implants was also measured to evaluate the binding activity against VEGF, which is a target antigen (FIG. 5B). It was calculated by the following equation, $$\text{Immunoreactivity (\%)} = \frac{\text{Concentration from } ELISA}{\text{Concentration from } SE \text{ by } HPLC} \times 100\%$$

and measured at 114.7 and 101.5% for extracts from 30 and 50% PLGA coated implants, which means the preparation of the implant and extraction process did not decrease immunoreactivity of bevacizumab. For the release samples, bevacizumab immunoreactivity was maintained between 83.0 and 111.5% for 30% PLGA coated one and between 89.0 and 105.4% for 50% PLGA coated one until day 28. On day 42, the immunoreactivity slightly decreased to 73.8 and 79.4%, respectively. Additionally, the far-UV CD spectra showed high conformational stability in the secondary structure of bevacizumab from protein powder, extracts from implants, and release samples (FIG. 5C). Immunoglobulin G1 (IgG1), which is a subclass of bevacizumab is known to have significant β-sheet structure characterized by broad negative peak at 218 nm in its far-UV CD spectrum [30], and all the spectra from each bevacizumab sample indicated insignificant changes in the secondary structure. Therefore, it is concluded that released soluble bevacizumab from the both coated implants in a sustained manner also maintained high levels of monomer content, immunoreactivity and secondary structure for six weeks.

CONCLUSIONS

In this study, bevacizumab was loaded PLGA implants to reduce its administration frequency. The presence of trehalose was able to prevent the antibody from aggregating in the solid protein powder at the weight ratio of 1.5:1 w/w or higher. This ratio was found to be a formulation sweet spot, which is high enough to stabilize the protein but not so high as to disrupt the release of the coated polymer. By coating the core implants with pure PLGA, higher loading (7.6-8.2%, w/w) and more continuous near zero-order release over 6 weeks were achieved without a high initial burst release in the formulations. The coating thickness was also adjusted to be thick enough to accomplish controlled release but not so thick to prevent release of water-soluble acids known to damage the protein [14]. Co-encapsulating trehalose and $MgCO_3$ as stabilizers also helped to achieve high total cumulative release (81.7-89.0%). Bevacizumab released from these coated implants maintained the monomer content well above 90% as well as excellent preservation of immunoreactivity, and secondary structure during the whole release period.

TABLE 1

Composition in 4 mL of Avastin ® solution.

| Composition | Weight (mg) | Weight percentage (%) |
|---|---|---|
| Bevacizumab | 100 | 27.1 |
| Trehalose dehydrate | 240 | 64.9 |
| Polysorbate 20 | 1.6 | 0.4 |
| Sodium phosphate, monobasic, monohydrate | 23.2 | 6.3 |
| Sodium phosphate, dibasic, anhydrous | 4.8 | 1.3 |

TABLE 2

Loading of implants prepared from bevacizumab powder with and without trehalose.

| Trehalose:bevacizumab in powder (w/w) | Theoretical loading (%) | Extracted loading (%) | Loading efficiency (%) |
|---|---|---|---|
| 2.4:1 | 3 | 2.8 ± 0.2 | 92.2 ± 5.0 |
|  | 6 | 6.0 ± 0.8 | 99.6 ± 12.7 |
|  | 10 | 9.9 ± 0.6 | 98.5 ± 6.3 |
|  | 15 | 14.5 ± 1.5 | 96.6 ± 10.3 |
| 0:1 | 15 | 9.0 ± 0.3 | 59.9 ± 2.3 |

Data reported as mean ± SD, n = 3

TABLE 3

Summary of in vitro cumulative release and aggregation behavior of bevacizumab from implants prepared from protein powder with and without trehalose.

| Trehalose:bevacizumab in powder (w/w) | Theoretical loading (%) | Cumulative release (%) | Soluble residue (%) | Non-covalent aggregate (%) | Covalent aggregate (%) | Recovery (%) |
|---|---|---|---|---|---|---|
| 2.4:1 | 3 | 57.0 ± 14.7 | 0 | 14.1 ± 4.5 | 0.9 ± 0.9 | 71.9 ± 17.7 |
| 0:1 | 15 | 12.9 ± 0.3 | 1.3 ± 2.3 | 40.3 ± 19.3 | 1.6 ± 1.7 | 56.2 ± 23.0 |

Data reported as mean ± SD, n = 3

TABLE 4

Loading of implants prepared from bevacizumab powder with the ratio of 1.5:1 w/w trehalose:bevacizumab.

| Trehalose:bevacizumab in powders | Theoretical loading (%) | Extracted loading (%) | Loading efficiency (%) |
|---|---|---|---|
| 1.5:1 | 3 | 2.7 ± 0.0 | 90.7 ± 0.9 |
|  | 6 | 5.6 ± 0.2 | 93.0 ± 3.5 |
|  | 10 | 9.2 ± 0.2 | 92.1 ± 2.3 |
|  | 15 | 14.1 ± 0.7 | 94.1 ± 4.9 |

Data reported as mean ± SD, n = 3

TABLE 5

Loading and diameter of uncoated and coated implants.

| Trehalose:bevacizumab in powders | PLGA concentration in coating (%, w/w) | Theoretical loading in core implants (%) | Extracted loading (%) | Diameter (mm) |
|---|---|---|---|---|
| 1.5:1 | Uncoated | 10 | 9.2 ± 0.2 [a] | 0.64 ± 0.02 |
|  | 10 |  | 9.0 ± 0.7 | 0.64 ± 0.01 |
|  | 30 |  | 8.2 ± 1.1 | 0.75 ± 0.01 |
|  | 50 |  | 7.6 ± 0.4 | 0.88 ± 0.01 |
|  | 50 | 15 | 10.8 ± 0.3 | N.D. [b] |
| 2.4:1 | 50 | 10 | 7.6 ± 0.8 | N.D. |

[a] Data reported as mean ± SD, n = 3.
[b] N.D. = not determined.

TABLE 6

Summary of in vitro cumulative release and aggregation behavior of bevacizumab from the coated implants prepared with 1.5:1 w/w trehalose:bevacizumab powder.

| PLGA concentration in coatings (% w/w) | Cumulative release (%) | Soluble residue (%) | Non-covalent aggregate (%) | Covalent aggregate (%) | Recovery (%) |
| --- | --- | --- | --- | --- | --- |
| 30 | 89.0 ± 3.6 | 0 | 7.8 ± 0.4 | 0.9 ± 0.3 | 97.7 ± 3.8 |
| 50 | 81.7 ± 7.6 | 0 | 8.9 ± 4.2 | 1.4 ± 1.6 | 91.9 ± 8.2 |

Data reported as mean ± SD, n = 3

Example 2—Evaluation in a Rabbit Retinal Leakage Model

Materials, preparation of antibody powder, and preparation of coated implants were as in Example 1.

Measurement of Antibody Loading in Implants

Implants (3-5 mg) were dissolved in 1 mL of acetone for 1 h and centrifuged to precipitate protein. PLGA dissolved in supernatant was removed and the protein pellet was washed with acetone and centrifuged three times more to remove residual PLGA. The pellet was then air-dried, reconstituted in 0.5 mL of PBST (phosphate buffered saline with 0.02% Tween 80, pH 7.4) at 37° C. overnight and analyzed by SE-HPLC. The mobile phase (0.182 M $KH_2PO_4$, 0.018 M $K_2HPO_4$, and 0.25 M KCl [pH 6.2]) was run at a flow rate of 0.5 mL/min through a gel column (TSK-GEL G3000SWx1; Tosoh Bioscience, Tokyo, Japan), and elution was monitored at 280 nm. The volume of injection was 50 μL, and the running time was 30 minutes. All samples were filtered through 0.45 am filter. Extracted loading was calculated by the following equation.

$$\text{Extracted loading (\%)} = \frac{\text{Weight of extracted antibody}}{\text{Weight of total implant}} \times 100$$

Examining the Sustained Exposure of PLGA Encapsulated Bevacizumab in Rabbit Eyes.

Anti-vascular endothelial growth factor (VEGF) efficacy test of PLGA encapsulated bevacizumab was performed in the rabbit VEGF-induced retinal leakage model (male Dutch Belted rabbits) by Ophthy-DS, Inc. (Kalamazoo, Mich.). The PLGA coated implants (0.5 cm long, 4.1-4.2 mg) encapsulating bevacizumab (~400 μg) were injected into rabbit vitreous using an 18G thin-wall needle. To compare with free bevacizumab, the same dose (400 g of bevacizumab) of Avastin® solution was injected into rabbit vitreous of the other group. On day 42, recombinant human VEGF (1000 ng) was injected into each eye to induce retinal leakage. On day 45, fluorescein angiography (FA) was performed, then the degrees of fluorescein leakage and tortuosity of retinal blood vessels were scored on 4-point scale from 0 to 4: 0=no leakage and straight major vessels with some tortuosity of smaller vessels; 1=increased tortuosity of major vessels and/or vessel dilation; 2=leakage between major vessels; 3=leakage between major and minor vessels, minor vessels still visible; 4=leakage between major and minor vessels, minor vessels not visible. Each rabbit eye has two opposite directional blood vessel groups on the retina, thus the two blood vessel groups in a single eye were evaluated separately. The bevacizumab implant and free bevacizumab groups had two rabbits per group and both eyes were tested. Consequently, each group had eight samples to be scored (n=8). Only one rabbit was tested for the untreated control group (n=4). On day 56, recombinant human VEGF (1000 ng) was injected into each eye of the bevacizumab implant group and two newly added untreated control rabbits. On day 59, fluorescent angiography (FA) was performed and the leakage scores were evaluated. For this time point, the previous untreated control and free bevacizumab groups were not tested since their retinal blood vessels were damaged.

Figure 7:
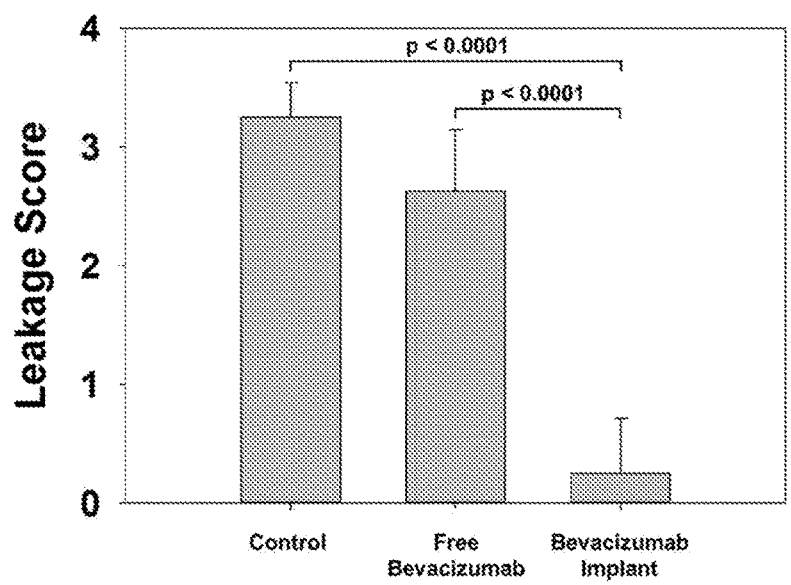
FIG. 7 shows Anti-VEGF efficacy of the PLGA coated implant encapsulating bevacizumab in the rabbit VEGF-induced retinal leakage model 6 weeks after implantation. Leakage scores (FIG. 7A, bars represent mean±SD) and fluorescent angiography (FA) images (FIG. 7B) of untreated control, free bevacizumab treated, and bevacizumab implant treated rabbits.
Figure 7:
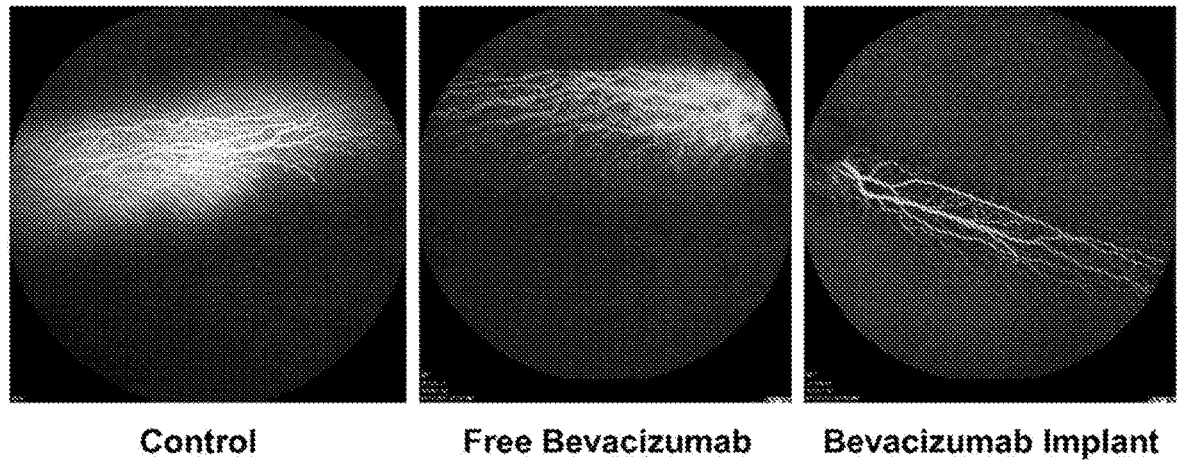
Figure 8:
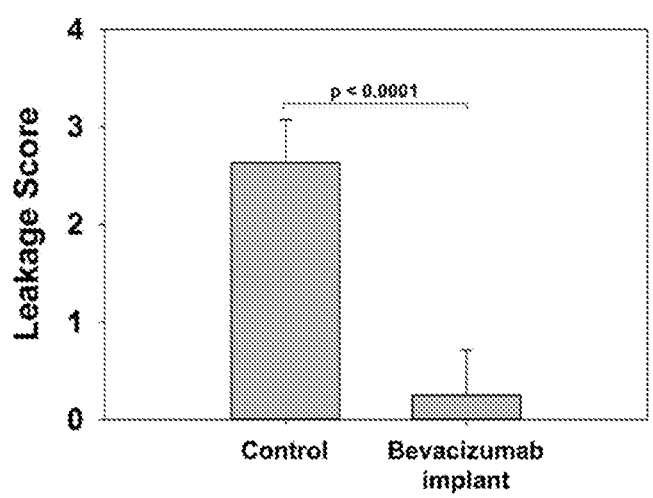
FIG. 8 shows Anti-VEGF efficacy of the PLGA coated implant encapsulating bevacizumab in the rabbit VEGF-induced retinal leakage model 8 weeks after implantation. Leakage scores (FIG. 8A, bars represent mean±SD) and FA images (FIG. 8B) of untreated control, and bevacizumab implant treated rabbits.
Figure 8:
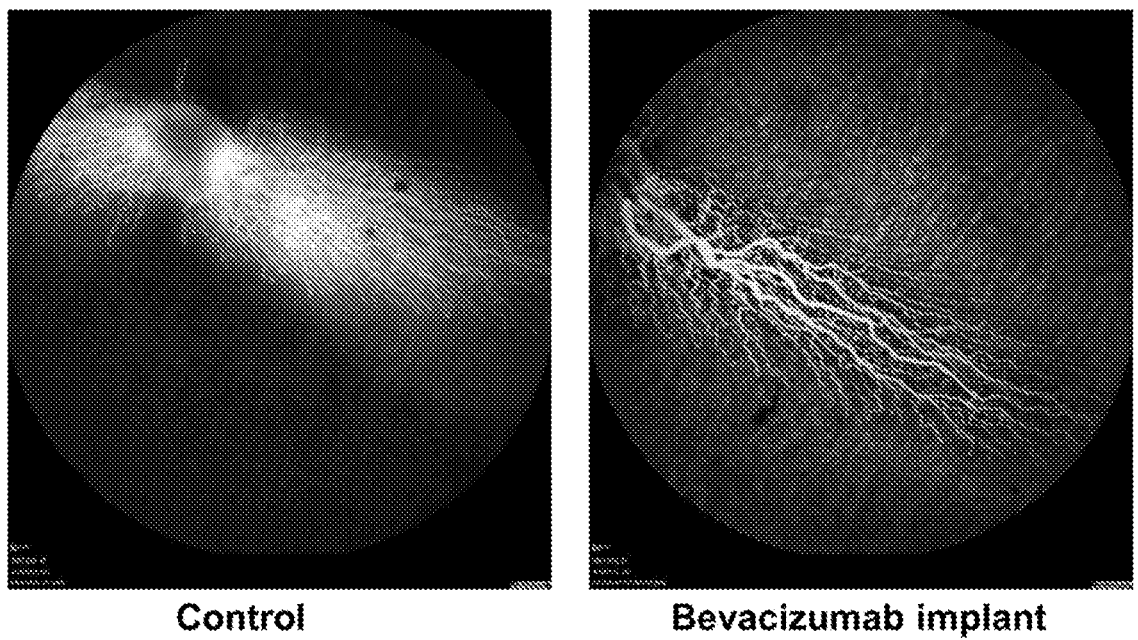

As shown in FIG. 7, our PLGA coated implant encapsulating bevacizumab protected retinal blood vessels from VEGF challenge 6 weeks after implantation. Leakage score (4-point scale) based on FA images of the bevacizumab implant group was only 0.25±0.46 (mean±SD, n=8) while the free bevacizumab group scored 2.63±0.52 (n=8) and the untreated control group scored 3.25±0.29 (n=4), see FIG. 7A. As shown in FIG. 7B, the leakage of the blood vessels in representative angiographs of soluble and control groups relative to the protected blood vessels in the implant group are clearly noticeable to the untrained eye. Eight weeks after implantation, the leakage score of the bevacizumab implant group was still only 0.25±0.46 (mean±SD, n=8) while the newly added untreated control group scored 2.63±0.44 (mean±SD, n=8) (FIG. 8A). Likewise, the leakage in representative angiograph of the untreated control group was significantly noticeable compared to the protective blood vessels in the implant group (FIG. 8B).

Example 3—In Vitro Release Study of PLGA-Encapsulated Bovine Serum Albumin (BSA)

Materials, preparation of BSA powder, and preparation of coated implants were as in Example 1 with slight modifications. For BSA powder, the same composition (trehalose:BSA=1.5:1, w/w) as applied in Example 1 was used with BSA as an additional model protein in place of bevacizumab. The resulting BSA powder was suspended into 50% (w/w) PLGA solution in acetone with 3% (w/w) $MgCO_3$ in a 2-mL centrifuge tube, then mixed and transferred into a 3-mL syringe. The suspension was extruded into silicone rubber tubing (I.D.=0.5 mm), then dried at room temperature for 48 h followed by vacuum drying at 40° C. and −23 in. Hg vacuum for an additional 96 h. The final dried implants were obtained by removal of silicone tubing. For coated implants, the obtained core implants were put back into silicone tubing (I.D.=0.8 mm) and 70% pure PLGA solution in acetone within a 3-mL syringe was extruded over the core implants to coat the surface and dried in vacuum oven at room temperature for 48 h and at 40° C. for an additional 96 h. Then, silicone tubing was removed and the final coated implants were cut for the following experiments.

Measurement of BSA Loading in Implants

Implants (2-3 mg) were dissolved in 1 mL of acetone for 1 h and centrifuged to precipitate proteins. PLGA dissolved in supernatant was removed and the protein pellet was washed with acetone and centrifuged three times more to remove residual PLGA. The pellet was then air dried, reconstituted in 0.5 mL of PBST (phosphate buffered saline with 0.02% Tween-80, pH 7.4) at 37° C. overnight and analyzed by Coomassie protein assay (Thermo Fisher Scientific, Waltham, Mass.). Extracted loading was calculated by the following equations.

$$\text{Extracted loading (\%)} = \frac{\text{Weight of extracted } BSA}{\text{Weight of total implant}} \times 100\%$$

In Vitro Release Study of BSA from Implants

Implants (0.5 cm long, 3-4 mg) were added in 1.5 mL centrifuge tubes with 1 mL of PBST and incubated at 37° C. without agitation. The release medium was replaced with fresh medium at each time point. The amount of released protein at each time point was measured by Coomassie protein assay and calculated as percentage of the released amount out of the extracted loading of soluble BSA.

Coated Implants with Pure PLGA for Sustained Release of BSA

Figure 9:
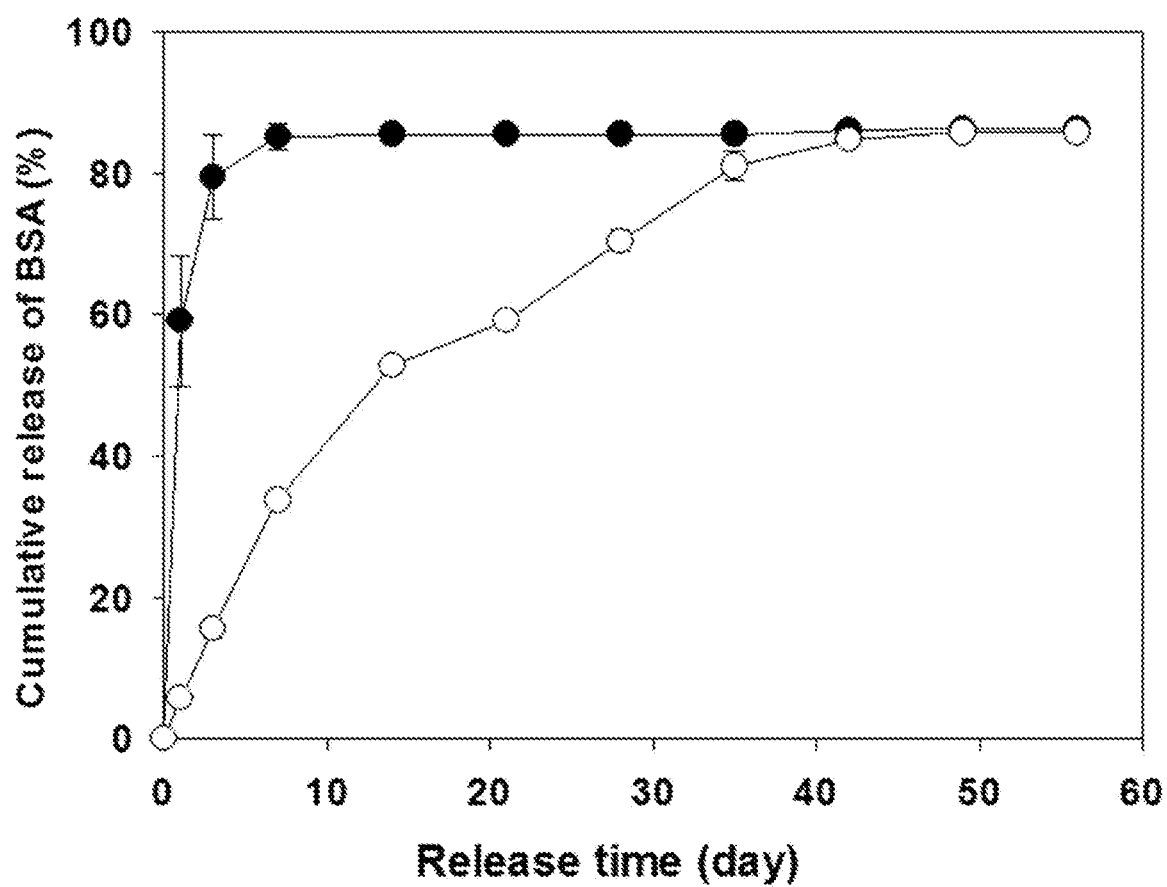
FIG. 9 shows in vitro release of bovine serum albumin (BSA) from uncoated (filled circles) and coated (open circles) cylindrical implants. Symbols represent mean±SD, n=3.

As expected from Example 1, the core implants with the extracted loading of 9.8±0.8% (mean±SD, n=3) released most of soluble BSA by day 7 and the total cumulative release by day 56 was 86.4±0.1% (closed circles in FIG. 9). By coating implants with pure PLGA, the coated implants with the extracted loading of 3.4±0.2% (mean±SD, n=3) demonstrated more sustained release, and similar total cumulative release (85.8±0.1%) (open circles in FIG. 9). Hence, one can conclude that this coating strategy might be useful toward developing sustained release formulations of numerous proteins and polypeptides.

What is claimed is:

1. A method of making an implant to deliver a monoclonal antibody to a tissue, comprising:
   a. providing a powder composition comprising the monoclonal antibody;
   b. combining the powder composition with a solution comprising a first biodegradable polymer containing lactic acid and/or glycolic acid repeat units in an organic solvent to make a suspension, wherein the suspension comprises the monoclonal antibody, the first biodegradable polymer, the organic solvent, a stabilizer comprising a water soluble saccharide, and a basic material, wherein the basic material has a solubility in water of $2 \times 10^{-2}$ M or lower at room temperature,
   C. drying the suspension to remove the organic solvent and form a core, wherein the core comprises about 5 to about 10 wt % of the monoclonal antibody, based on the total weight of the core; and
   d. applying a coating of a second biodegradable polymer on the core effective to provide an implant having a release profile characterized by:
   (i) a release of less than 20% of the total monoclonal antibody in the implant during the first 24 hours, relative to the total amount of monoclonal antibody in step (c), after incubating the implant with 1 mL of phosphate buffered saline with 0.02% polysorbate 80 at 37° C. with no agitation; and
   (ii) a continuous release of at least 80% of the total monoclonal antibody in the implant over 42 days, relative to the total amount of the monoclonal antibody in step (c), after incubating the implant with 1 mL of phosphate buffered saline with 0.02% polysorbate 80 at 37° C. with no agitation;
   wherein the second biodegradable polymer comprises lactic acid and/or glycolic acid repeat units.

2. The method according to claim 1, wherein at least one of the first and the second biodegradable polymer is poly (lactic-co-glycolic acid).

3. The method according to claim 2, wherein the molar ratio of lactic to glycolic acid in the biodegradable polymer is 1:1.

4. The method according to claim 2, wherein the first biodegradable polymer is the same as the second biodegradable polymer.

5. The method according to claim 1, wherein the stabilizer is a disaccharide.

6. The method according to claim 5, wherein the disaccharide comprises trehalose.

7. The method according to claim 1, wherein the monoclonal antibody comprises bevacizumab.

8. The method according to claim 5, wherein the weight ratio of soluble saccharide to monoclonal antibody is from about 0.3:1 to about 2:1.

9. The method according to claim 1, wherein the solution of the first biodegradable polymer comprises 10% to 50% by weight of the first biodegradable polymer.

10. The method according to claim 1, comprising extruding the suspension into a conduit before drying.

11. The method according to claim 10, wherein the conduit is silicone tubing.

12. The method according to claim 1, wherein the powder composition comprises the water soluble saccharide before combining with the solution.

13. The method according to claim 1, wherein the solution comprises the basic material before combining with the powder composition.

14. The method according to claim 10, wherein applying the coating on the core comprises extruding a solution comprising a non-aqueous solvent and the second biodegradable polymer over the core and removing the solvent in situ.

15. The method according to claim 13, wherein the basic material comprises magnesium carbonate, magnesium hydroxide, or zinc carbonate.

16. The method according to claim 1, wherein the monoclonal antibody binds vascular endothelial growth factor with an affinity of $1 \times 10^{31\ 6}$ M or greater.

17. A method of making an implant to deliver bevacizumab to a tissue, comprising:
   a. providing a powder composition comprising bevacizumab and trehalose, wherein the weight ratio of trehalose to bevacizumab is from about 0.3:1 to about 2:1;
   b. combining the powder composition with a solution of poly (lactic-co-glycolic acid), in an organic solvent to make a suspension, wherein the suspension also comprises a basic material having a solubility in water of $2 \times 10^{-2}$ M or lower at room temperature;
   c. extruding the suspension into a conduit;
   d. drying the suspension in the conduit to remove the organic solvent and form an elongated core in the conduit, wherein the elongated core comprises about 5 to about 10 wt % of the monoclonal antibody, based on the total weight of the core; and
   e. applying a coating on the core by extruding a solution comprising a solvent and poly (lactic-co-glycolic acid) over the core and removing the solvent from the solution;

wherein the coating is effective to provide an implant having a release profile characterized by:
(i) a release of less than 20% of the total bevacizumab in the implant during the first 24 hours, relative to the total amount of bevacizumab in step (d), after incubating the implant with 1 mL of phosphate buffered saline with 0.02% polysorbate 80 at 37° C. with no agitation; and
(ii) a continuous release of at least 80% of the total bevacizumab in the implant over 42 days, relative to the total amount of the bevacizumab in step (d), after incubating the implant with 1 mL of phosphate buffered saline with 0.02% polysorbate 80 at 37° C. with no agitation.

18. The method according to claim 17, further comprising removing the core from the conduit and cutting the core into a plurality of cylindrical implants.

19. The method according to claim 17, wherein the suspension comprises 1% to 15% by weight of bevacizumab.

20. The method according to claim 17, wherein the basic material comprises magnesium carbonate, magnesium hydroxide, or zinc carbonate.

21. A solid implant for delivering monoclonal antibodies in the form of a cylinder having a diameter of 0.1 to 10 mm and having a length along the cylindrical axis of 1 to 20 mm, the implant comprising a cylindrical inner portion comprising a cylindrical surface and two ends and a coating on the cylindrical surface of the cylindrical inner portion,
wherein the cylindrical inner portion comprises a water soluble saccharide, a monoclonal antibody provided in an amount of about 5 to about 10 wt %, based on the total weight of the cylindrical inner portion, a basic compound having a solubility in water of $2\times10^{-2}$ M or lower at room temperature, and PLGA, and
the coating comprises PLGA and is effective to provide an implant having a release profile characterized by:
(i) a release of less than 20% of the total monoclonal antibody in the implant during the first 24 hours, relative to the total amount of monoclonal antibody initially provided in the implant, after incubating the implant with 1 mL of phosphate buffered saline with 0.02% polysorbate 80 at 37° C. with no agitation; and
(ii) a continuous release of at least 80% of the total monoclonal antibody in the implant over 42 days, relative to the total amount of the monoclonal antibody initially provided in the implant, after incubating the implant with 1 mL of phosphate buffered saline with 0.02% polysorbate 80 at 37° C. with no agitation.

22. The implant according to claim 21, wherein the impant has a loading of monoclonal antibody greater than 5% by total weight of the implant.

23. The implant according to claim 21, wherein the monoclonal antibody retains at least 80% of its activity after incubating the implant with 1 ml of phosphate buffered saline with 0.02% polysorbate 80 at 37 ° C. with no agitation over 42 days, as measured by ELISA.

24. The implant according to claim 21, wherein the water-soluble saccharide comprises trehalose.

25. The implant according to claim 21, wherein there is no coating on the two ends of the cylindrical inner portion.

26. An implant according to claim 21, wherein the monoclonal antibody comprises bevacizumab.

27. The implant according to claim 21, wherein the implant has a loading of monoclonal antibody greater than 5% by total weight of the implant, and the antibody retains at least 80% of its activity during in vivo use, as determined by ELISA during in vitro testing.

28. A method of treating wet age related macular degeneration in a patient, comprising inserting an implant according to claim 26 into the eye of the patient.

29. A method of treating wet macular degeneration in a patient, comprising inserting an implant according to claim 21 into the eye of the patient.

30. A method of treating wet macular degeneration in a patient, comprising inserting an implant according to claim 27 into the eye of the patient.

31. A method of making an implant to deliver a monoclonal antibody to a tissue, comprising:
a. providing a powder composition comprising the monoclonal antibody;
b. combining the powder composition with a mixture comprising a first biodegradable polymer containing lactic acid and/or glycolic acid repeat units, wherein the combined mixture comprises the monoclonal antibody, the first biodegradable polymer, a stabilizer comprising a water soluble saccharide, and a basic material, wherein the basic material has a solubility in water of $2\times10^{41}$ M or lower at room temperature,
c. forming the combined mixture into a uniform dry polymer matrix in a shape suitable for drug delivery, wherein the monoclonal antibody is provided in an amount of about 5 to about 10wt %, based on the total weight of the dry polymer matrix; and
d. applying a coating of a second biodegradable polymer on the dry polymer matrix; wherein the coating is effective to provide an implant having a release profile characterized by:
(i) a release of less than 20% of the total monoclonal antibody in the implant during the first 24 hours, relative to the total amount of monoclonal antibody in step (c), after incubating the implant with 1 mL of phosphate buffered saline with 0.02% polysorbate 80 at 37° C. with no agitation; and
(ii) a continuous release of at least 80% of the total monoclonal antibody in the implant over 42 days, relative to the total amount of the monoclonal antibody in step (c), after incubating the implant with 1 mL of phosphate buffered saline with 0.02% polysorbate at 37° C. with no agitation;
wherein the second biodegradable polymer comprises lactic acid and/or glycolic acid repeat units.

32. The method of claim 31, comprising applying the coating at the same time that the uniform dry polymer matrix is formed.

33. The method according to claim 1, wherein the core, prior to coating, has an initial burst of 60% of the monoclonal antibody after 24 hours of incubation in a phosphine buffered saline with polysorbate 20 (PBST) solution at 37° C., without agitation.

34. The method according to claim 17, wherein the cylindrical inner portion, prior to coating, has an initial burst of 60% of the monoclonal antibody after 24 hours of incubation in a phosphine buffered saline with polysorbate 20 (PBST) solution at 37° C., without agitation.

35. The method according to claim 31, wherein the dry polymer matrix, prior to coating, has an initial burst of 60% of the monoclonal antibody after 24 hours of incubation in a phosphine buffered saline with polysorbate 20 (PBST) solution at 37° C., without agitation.

* * * * *